(12) United States Patent
Eiselen

(10) Patent No.: US 6,833,486 B1
(45) Date of Patent: Dec. 21, 2004

(54) CERAMIC WOUND TREATMENT DEVICE

(75) Inventor: Ernst R. Eiselen, Mtunzini (ZA)

(73) Assignee: D & E Cryo CC, Mtunzini (ZA)

(*) Notice: Subject to any disclaimer, the term of this patent is extended or adjusted under 35 U.S.C. 154(b) by 0 days.

(21) Appl. No.: 09/959,826

(22) PCT Filed: May 8, 2000

(86) PCT No.: PCT/IB00/00592
§ 371 (c)(1), (2), (4) Date: Dec. 19, 2001

(87) PCT Pub. No.: WO00/69480
PCT Pub. Date: Nov. 23, 2000

(30) Foreign Application Priority Data

May 12, 1999 (ZA) .............................. 99/3273
Sep. 23, 1999 (ZA) .............................. 99/6118

(51) Int. Cl.[7] .......................... A61F 13/00; A61K 9/70
(52) U.S. Cl. ........................................ 602/48; 424/443
(58) Field of Search ................................ 424/443–449, 424/484–489; 602/43, 48; 604/304

(56) References Cited

U.S. PATENT DOCUMENTS 3,842,830 A * 10/1974 Hargest ........................ 602/43
5,000,746 A * 3/1991 Meiss .......................... 604/304
5,834,008 A * 11/1998 Greenspan et al. .......... 424/443

FOREIGN PATENT DOCUMENTS

| DE | 26 52 088 | * | 5/1978 |
| WO | 90/08470 | * | 8/1990 |
| WO | WO 00/15167 | * | 3/2000 |

* cited by examiner

Primary Examiner—John J. Calvert
Assistant Examiner—Linh Truong
(74) Attorney, Agent, or Firm—Nixon & Vanderhye P.C.

(57) ABSTRACT

This invention relates to a ceramic wound treatment device and to a method of treating a wound using such device. The treatment device comprises a plurality of separate inert porous ceramic particles which are contained in a permeable tea-bag type container. The particles have a porosity of between 25% and 85%, preferably 75% and the pores have diamters in the range of between 0.4 to 30 micrometers. The pores are cellular in nature and are interconnected by blowholes. The particles are manufactured by pulverising an inert microporous ceramic body and removing fine powder from the particles, such that the particles have a diameter range of between 45 and 300 micrometers.

10 Claims, 1 Drawing Sheet

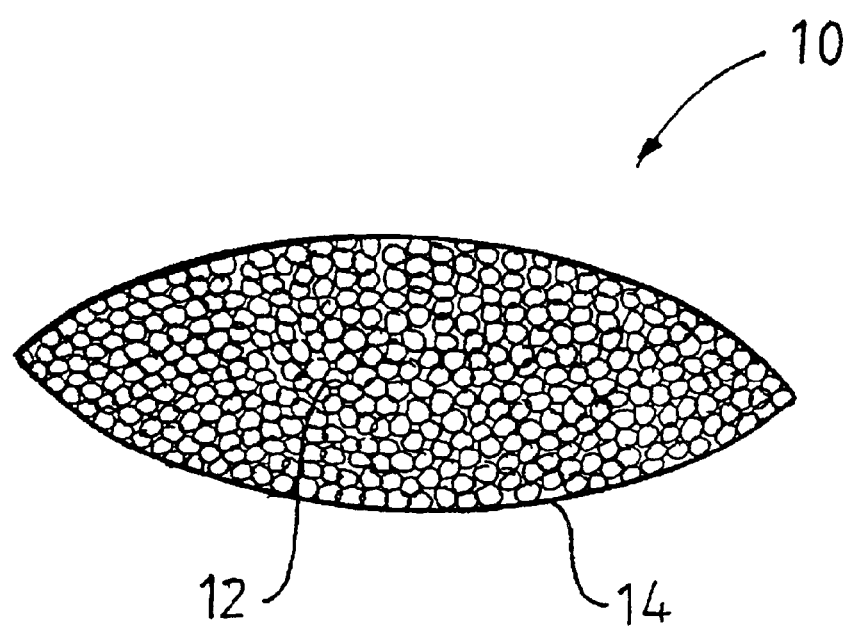

CERAMIC WOUND TREATMENT DEVICE

This invention relates to a ceramic wound treatment device and to a method of treating a wound using such device.

U.S. Pat. No. 3,842,830 discloses a surgical dressing comprising impermeable high silica glass microparticles. The particles are applied directly to the wound. A disadvantage of the surgical dressing is that it is saturated relatively easily, so that a substantial amount of microparticles have to be applied to a wound to have a desirable effect.

U.S. Pat. No. 5,000,746 discloses a covering for wounds comprising a permeable web, which remains flexible during use. The web is made up from a plurality of individually shaped elements connected by connecting members into a network, and having, at least on the surface, a layer of ceramic or glass. Alternatively, the covering comprises a base, such as a mat, web or fabric, provided with a glass or ceramic layer. Column 3 lines 14 to 16 of the specification states that "The bodies or elements may be liquid impermeable or they may be porous, and they can suitably be made of a bioinert material, such as aluminium oxide ($Al_2O_3$)." It is therefore clear that the porosity of the elements is not an essential feature of the invention disclosed in that specification and that impermeable glass particles work equally well.

A disadvantage of a covering of this type is that it is relatively expensive and difficult to manufacture. Particularly, it is onerous to shape the individual particles and to link the particles together.

OBJECT OF THE INVENTION

It is therefore an object of the present invention to provide a ceramic wound treatment device and a method of treating a wound using such device with which the aforesaid disadvantages can be overcome or at least minimised and to provide an effective alternative wound treatment device to conventional wound dressings.

SUMMARY OF THE INVENTION

According to a first aspect of the invention there is provided a wound treatment device comprising a plurality of separate porous ceramic particles.

The particles may be contained in a permeable container.

The container may comprise a tea-bag type envelope. Preferably the envelope is of Vilene™.

The ceramic particles may be inert.

The ceramic particles may have a porosity of between 25% and 85%, preferably 75%.

The pores of the particles may have diameters in the range of between 0.3 to 30 micrometers.

The pores may be cellular in nature.

The pores may be interconnected by blow-holes.

The arrangement may be such that the pores of the ceramic particles apply a capillary suction force to the wound area, thus continuously draining fluid from the area.

The particles may be manufactured by pulverising an inert microporous ceramic body and removing fine powder from the particles.

The particles may have a diameter range of between 45 and 300 micrometers.

According to a second aspect of the invention there is provided a method of treating a wound, the method including the steps of applying to such wound a ceramic wound treatment device as hereinbefore described.

BRIEF DESCRIPTION OF DRAWING

FIG. 1 a cross-sectional and view of ceramic wound treatment device.

DETAILED DESCRIPTION OF THE INVENTION

The invention will now be described further by way of non-limiting examples and with reference to the enclosed drawing, FIG. 1 which is a cross-sectional end view of a ceramic wound treatment device 10 (CWTD) according to a preferred embodiment of the invention. The CWTD 10 is prepared by a method including the steps of:

milling solid petalite ($LiAlSi_4O_{10}$) into powder (1 micrometer diameter particles);

adding a combustible substance to the powder;

mixing the powder with water to form a paste or slurry;

drying out the paste to form a ceramic aggregate;

firing the ceramic aggregate to a temperature of 1200° C. to form an inert microporous solid ceramic body having pore sizes of between 0.3 to 30 micrometers;

pulverising the ceramic body into particles 12 having a diameter of between 45 and 300 micrometers;

removing fine powder and ceramic dust from the particles 12;

disposing the particles in a tea-bag type Vilene™ envelope 14; and sealing the envelope 14.

Instead of drying out the paste to form an aggregate, the paste can also be spray-dried to form spherical particles of suitable sizes, which are then sintered at 1200° C. After the preparation procedure, the ceramic particles are to be kept dry.

The standard wound treatment protocol, irrespective of the type of wound being treated, is as follows:

open the wound by removing any soiled bandages that may previously have been applied to the wound;

optionally applying normal saline (0.9 %) to the wound;

optionally cover the wound with a single layer of gauze;

apply the CWTD to the wound; and fasten the CWTD with a bandage, adhesive strip, or transparent cover.

EXAMPLE 1

Treatment of Post-Infective Venous Stasis Ulcer

An 84-year old male patient with poor peripheral circulation in both legs, due to large varicose veins and old age, was subjected to treatment with the CWTD according to the invention. He had developed a large, sloughing ulcer due to severe cellulitis of his leg. It had to be surgically debrided and the resulting ulcer was still very septic and sloughing after the surgery. The surgeon anticipated further surgical treatment. The patient was not responding to systematic treatment with quinolone antibiotics and daily povidone iodine dressings. It was feared that the patient would lose either his leg or his life.

The patient was treated according to the above standard wound treatment protocol. Within 48 hours after treatment was started, the wound changed from a clearly catabolic state into an anabolic state with granulation tissue forming and slough coming off. The wound started losing its bad odour, despite the fact that it was still pouring out a green coloured pus. Pain from the wound started to diminish and it was clear that the general condition of the patient was also improving.

The CWTD's were applied without wiping or swabbing the wound clean.

The standard protocol was used as follows:

the wound was opened by removing the CWTD every morning;

a single layer of dry, woven cotton gauze was applied on the wound;

the CWTD was applied on top of the gauze and secured into place by a single strip of 10 mm wide adhesive paper tape;

the CWTD was covered with a protective elastic cotton bandage in two layers; and elastic, compressive stockings were dressed on top of the CWTD every day as this patient had clinically significant varicose veins.

Results

The CWTD deodorised the wound virtually entirely since the start of treatment.

The wound became pain free after 30 days.

The rate of healing was above all expectations, especially in the presence of pathogenic bacteria actively forming pus;

Despite continuing deterioration in his general condition and recuperative powers, the wound proceeded to heal over 8 months. The wound healed from dimensions of 95 mm×45 mm×18 mm to a circular wound of 18 mm in diameter and less than 1 mm deep when the patient died of combined cardiac and renal failure, unrelated to the wound.

EXAMPLE 2

Treatment of Impetigo Ulcers.

A 15 year old male with relatively large leg and foot ulcers due to typical lesions of staphylococcal impetigo, was treated with the CWTD according to a modified wound treatment protocol, as set out below. The lesions were about six days old when first seen. They had previously been treated by applying Mercurochrome™ tincture for a few days. It was decided to do a comparative treatment by applying a povidone iodine ointment to the ulcer on the shin and the CWTD according to the invention to the ulcer on the toe.

The CWTD's were applied without wiping or swabbing the ulcer on the toe. A modified wound treatment protocol was used as set out below:

the ulcer was opened by removing existing dressings;

a single layer of dry, woven cotton gauze was applied on the ulcer;

the CWTD was applied on top and secured into place by a single strip of 10 mm wide adhesive paper tape;

the CWTD was then covered with a protective elastic cotton bandage in two layers;

The CWTD was the only mode of topical treatment on the toe.

Results

Both ulcers were healing well at the first follow up on day 6, but only the toe ulcer had healed by day 26. The leg ulcer was still being treated by topical iodine and was not showing signs of healing. The patient requested on day 26 to have the CWTD applied to the shin ulcer as well. On day 26 (after being without the CWTD for 5 days) the patient returned with a very septic shin lesion. Interestingly enough the defect had partially closed despite the new sepsis. An initial 5 day course of oral treatment, comprising 2 cortrimoxazole tablets twice a day and Asprin (600 mg) was administered. After day 5, only topical treatment was applied. The patient defaulted twice on treatment and was without CWTD for 3 days the first time and for 5 days the second time. The shin wound healed uneventfully within 26 days from the start of the treatment.

EXAMPLE 3

Treatment of Recurrent Venous Stasis Ulcer.

A 72 year old female patient with pour peripheral circulation in both legs due to varicose veins, obesity and age, was subjected to treatment. She had an ulcer in the same position a year before. Minor trauma started the present ulcer 6 weeks prior to this first visit.

The patient was treated according to the standard wound treatment protocol as follows:

the wound was opened by removing dressings;

a single layer of dry, woven cotton gauze was applied to the wound;

the CWTD was applied on top and secured into place by a single layer of 10 mm wide adhesive paper tape. The CWTD's were applied without wiping or swabbing the wound clean;

the CWTD's were covered with a protective elastic cotton bandage in two layers;

during the last three weeks of treatment, the CWTD's were left in place for 5 days at a time.

No antibiotics were administered either topically or systemically.

The patient could not afford an elastic compressive stocking as would have been indicated for use in her case.

The patient lived in a hut made of sticks and mud with very rudimentary ablution facilities.

Results

The CWTD deodorised the wound almost completely.

The rate of healing was above all expectations, especially in the presence of old scar tissue.

The wound was completely healed with good quality scar tissue by day 58. On follow up after one year, the scar had remained stable with surprisingly good aesthetic appearance.

EXAMPLE 4

Treatment of Septic Post-Operative Wound

A 34 year old female patient who had delivered her second child by Caesarean section three weeks before, were treated with the CWTD. A puncture wound on the side of the Pfannenstiel incision did not heal and was continually oozing serous fluid. The patient had been treated with povidone iodine dressings after first cleaning the wound with Eusol™.

The wound was treated according to the standard protocol. The patient treated the wound at home and continued to do her home work as usual.

Initially the wound healed well, but after about 9 days a second wound, adjacent to the first lesion opened up on the scar. The skin now appeared to have developed an allergy to the Micropore™ adhesive tape. It was decided to stop all treatment for 48 hours and then to resume without the adhesive tape. A moderate strength topical cortisone cream was applied to the irritated skin during these two days. Upon resumption of treatment with the CWTD, the skin immediately became irritated again, when the patient realised that it was the hypochloride solution that was causing the irritation, and thereafter used normal saline for wetting the wounds.

Results

Both wounds then proceeded to heal uneventfully and both wounds were healed by day 34.

EXAMPLE 5

Treatment of Venomous Bite Wound

A 39 year old female patient with a venomous bite (possibly a spider) on the sole of her foot was treated with the CWTD. The patient was first seen on day 6 after the injury. The lesion had a small area of central necrosis about 5 mm in diameter and 3 mm deep with an area of hyperaemia, about 25 mm by 35 mm, where the skin looked injured.

Treatment with the CWTD commenced on day 6, according to the standard treatment protocol. No other treatment was used.

Results

The patient returned for follow up on day 10 of treatment. The lesion showed the following features:

the dead skin had come off to its full extent;

the base was completely clean and covered by healthy granulation tissue; and re-epithelialisation was in rapid progress.

The patient returned finally on day 24 of treatment with the lesion completely closed and no further treatment was required. The patient continued to work throughout her treatment and had only mild discomfort form the slightly bulky CWTD on the bottom of her foot.

EXAMPLE 6

A 25 year old male patient who was involved in a car accident was furthermore treated with the CWTD. He had sustained an injury to his left buttock area extending from the edge of the gluteal fold into the external sphincter of the anus. A laceration extended 5 cm laterally from the lower edge of the injury. The sphincter defect was repaired surgically in a nearby hospital. The repair was successful. The patient declined to have a colostomy done to cut off the faecal stream from passing over the injured area. He rather opted to see if the wound would heal without such drastic measures. The patient had no medical insurance and asked to be discharged on day 3 after the repair. The patient began treatment with CWTD on day 8 of the injury.

The CWTD was applied twice per day, after a 5-minute sitz bath in diluted Savlon™.

Results

By the $5^{th}$ day of use of the CWTD, the wound showed good granulation and de-sloughing. The patient was out of bed by this time and his pain was well controlled by no more than moderate strength oral analgesics once or twice per day. His wound was now easily treated at home. On day 18 of treatment with the CWTD, the wound started showing rapid healing, good quality granulation tissue and a steadily advancing edge of good quality skin covering the defect.

The patient went back to work on day 20 of treatment and continued to apply the CWTD twice per day following the standard treatment protocol. The wound of the patient was completely healed after 42 days of treatment. The wound remained stable after one year with minimum scarring after 6 months. The patient is fully continent after treatment.

CONCLUSION

The following observations are common with patients treated with the CWTD's according to the invention:

The wound area heals visibly despite the presence of adverse elements such as pathogenic bacteria and dead tissue (slough);

Excess fluids and bad odours are removed;

The patients generally experience less pain or cessation of pain altogether from their wounds;

The treatment produces similar results irrespective of the cause of the wound;

The CWTD's work well in the absence of aseptic application techniques.

The mode of application is simple and easy to understand and the wounds can therefore be treated by the patients themselves or by lay care givers in the home environment or in an active work environment.

The CWTD's are able to allow wounds to heal irrespective of the cause or location of the wound, the presence of superficial pathogenic infective agents, the age of the wound or previously applied treatments.

Furthermore, the healing process can proceed irrespective of the level of literacy, social class or age of the patient, his/her physical circumstances, the availability of trained care givers or patient expectations and, all of this at home.

The following types of ulcers and wounds were treated thus far:

septic post infective lower leg ulcers;

ulcers of impetigo;

varicose and venous stasis ulcers of legs;

venomous bite ulcers;

lacerations too old to suture;

septic post- operative wounds;

septic para-unguinal (big toe) lesions;

newly sutured lacerations—(much better cosmetic results seen);

dog bites;

dehiscence of post operative wound;

septic diabetic ulcers;

post faschiotomy wound;

tissue loss;

post cryotherapy (liquid nitrogen therapy of skin lesions);

bum wounds; and decubitus ulcers.

The applicant believes that the large surface area and the accompanying capillary suction forces caused by the pores of the ceramic particles contribute to the effectiveness of the wound treatment device according to the invention in the treatment of wounds and the like. By continuous siphoning of the excess wound exudate, the ballanced order of cell signals is restored and wound healing optimised irrespective of the cause of the wound or the stage at which the treatment was started.

It will be appreciated that variations in detail are possible with a ceramic wound treatment device, according to the invention, without departing from the scope of the appended claims.

What is claimed is:

1. A wound treatment device comprising a plurality of separate porous ceramic particles having a porosity of between 25% and 85%, the pores of the particles being interconnected by blow-holes.

2. A wound treatment device according to claim 1 wherein the particles are contained in a permeable container.

3. A wound treatment device according to claim 2 wherein the container comprises a tea-bag type envelope.

4. A wound treatment device according to claim 1 wherein the ceramic particles are inert.

5. A wound treatment device according to claim 1 wherein the ceramic particles have a porosity of 75%.

6. A wound treatment device according to claim 1 wherein the pores of the particles have diameters in the range of between 0.3 to 30 micrometers.

7. A wound treatment device according to claim 1 wherein the pores are cellular in nature.

8. A wound treatment device according to claim 1 wherein the particles are manufactured by pulverizing an inert microporous ceramic body and removing fine powder from the particles.

9. A wound treatment device according to claim 1 wherein the particles have a diameter of between 45 and 300 micrometers.

10. A method of treating a wound, the method including the steps of applying to such a wound a ceramic wound treatment device according to claim 1.

* * * * *